United States Patent
Friedlander et al.

(10) Patent No.: US 6,866,821 B2
(45) Date of Patent: Mar. 15, 2005

(54) AUTOMATIC DIAGNOSTIC APPARATUS

(75) Inventors: Uri Friedlander, London (GB); Neville Coupe, West Sussex (GB); Fabio Lissandrello, Milan (IT); Paola Casalin, Milan (IT); Patricia Connolly, Glasgow (GB)

(73) Assignee: Byk Gulden Italia S.p.A., Cormano (IT)

( * ) Notice: Subject to any disclaimer, the term of this patent is extended or adjusted under 35 U.S.C. 154(b) by 0 days.

(21) Appl. No.: 10/642,498

(22) Filed: Aug. 18, 2003

(65) Prior Publication Data

US 2004/0108225 A1 Jun. 10, 2004

Related U.S. Application Data

(63) Continuation of application No. 09/155,406, filed on Dec. 2, 1998, now abandoned.

(30) Foreign Application Priority Data

| Mar. 29, 1996 | (GB) | 9606728 |
| Nov. 1, 1996 | (GB) | 9622853 |
| Mar. 13, 1997 | (GB) | 9705243 |

(51) Int. Cl.[7] .................. G01N 35/00; G01N 27/26
(52) U.S. Cl. .................. 422/72; 422/68.1; 422/82.01; 204/403.01; 435/287.2; 436/45; 436/177
(58) Field of Search ............... 422/56, 57, 58, 422/61, 62, 68.1, 72, 82.01, 100, 102; 436/45, 63, 177, 178; 435/287.2, 287.6, 287.9; 204/409, 400, 403.01

(56) References Cited

U.S. PATENT DOCUMENTS

| 484,887 A | * | 7/1892 | Galle et al. ............... 422/65 |
| 3,841,838 A | * | 10/1974 | Natelson ................... 23/259 |
| 4,490,235 A | * | 12/1984 | Calzi ......................... 204/409 |
| 4,640,821 A | * | 2/1987 | Mody et al. ............... 422/81 |
| 4,654,127 A | * | 3/1987 | Baker et al. ............. 204/1 T |
| 4,678,752 A | * | 7/1987 | Thorne et al. ............ 435/291 |
| 4,708,940 A | * | 11/1987 | Yoshida et al. ............ 436/45 |
| 4,814,144 A | * | 3/1989 | Edelmann et al. ......... 422/102 |
| 4,854,933 A | * | 8/1989 | Mull ........................... 494/38 |
| 4,927,502 A | * | 5/1990 | Reading et al. ........ 204/153.1 |
| 4,974,592 A | | 12/1990 | Branco ...................... 128/635 |
| 5,188,583 A | * | 2/1993 | Guigan ....................... 494/43 |
| 5,399,256 A | * | 3/1995 | Bohs et al. ................ 204/409 |
| 5,571,396 A | * | 11/1996 | Cormier et al. ........... 204/418 |
| 5,837,199 A | * | 11/1998 | Dumschat ................ 422/68.1 |
| 5,958,791 A | * | 9/1999 | Roberts et al. ............ 436/514 |
| 6,051,392 A | * | 4/2000 | Ikeda et al. ................. 435/25 |
| 6,113,762 A | * | 9/2000 | Karube et al. ............ 204/403 |

FOREIGN PATENT DOCUMENTS

| EP | 223002 A | * | 9/1986 | G01N/35/00 |
| EP | 0 352 689 A1 | | 7/1989 | |
| EP | 0 359 049 A2 | | 8/1989 | |
| GB | 2289339 A | * | 11/1995 | G01N/33/543 |
| JP | 2110363 | * | 4/1990 | G01N/27/327 |
| WO | WO 90/01700 | | 7/1989 | |
| WO | WO 92/05449 | | 9/1991 | |
| WO | WO 94/19684 | | 2/1994 | |
| WO | WO 95/02189 | | 6/1994 | |

* cited by examiner

*Primary Examiner*—Maureen M. Wallenhorst
(74) *Attorney, Agent, or Firm*—Jacobson Holman PLLC

(57) ABSTRACT

Automatic diagnostic apparatus includes: a controller for controlling operation of the apparatus and for processing data; a sensing system operably connected to the controller for performing an assay, preferably an electrochemical assay (more preferably an electrochemical immunoassay), of a sample and communicating data from the assay to the controller; voltage supply means for applying a potential differential to the sensing system; and output means for communicating processed data to a user.

9 Claims, 12 Drawing Sheets

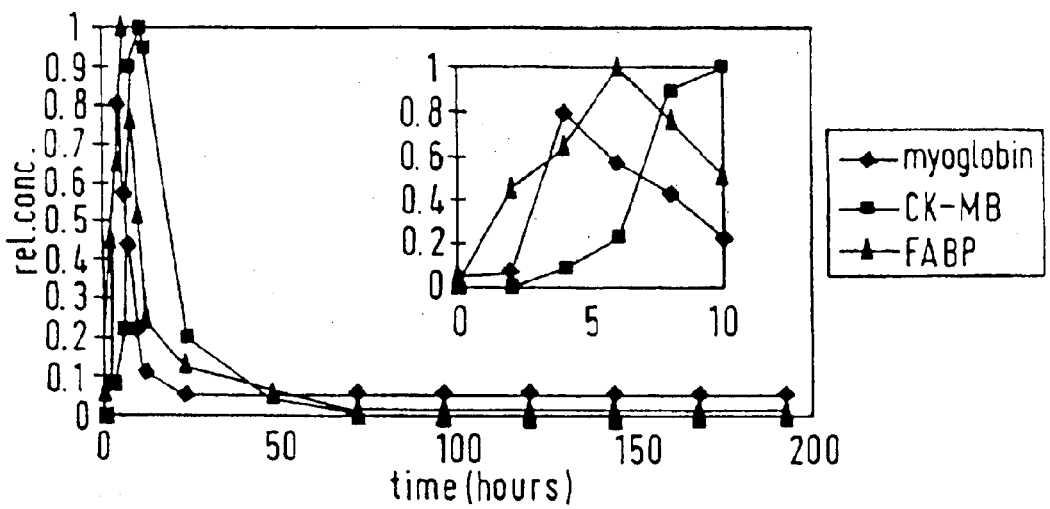
FIG. 14  first markers-AMI
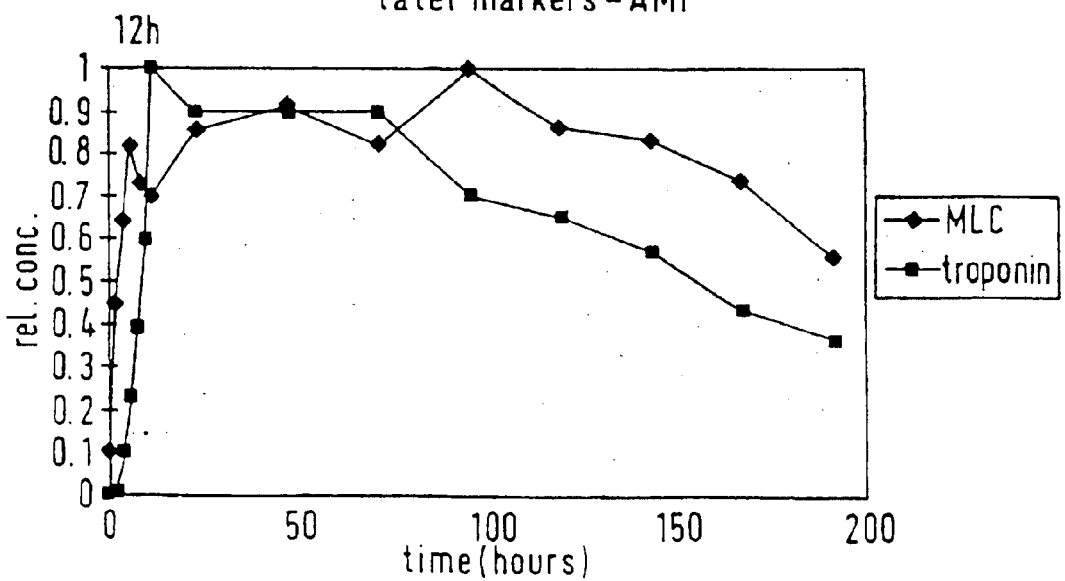
FIG. 15  later markers-AMI

AUTOMATIC DIAGNOSTIC APPARATUS

This is a continuation of application Ser. No. 09/155,406 filed Dec. 2, 1998 now abandoned.

This invention relates generally to an automatic diagnostic apparatus.

When a patient is treated by a physician, it is not uncommon for the physician to take samples of body fluids to be sent on to a laboratory for analysis. The testing often has to be done manually and thus, inevitably, some delay is incurred in the processing of these samples which also delays the point at which the results can be communicated to the patient.

Even in Hospitals, where the condition of the patients can be extremely serious, the samples still have to be sent away to an "in-house" laboratory for testing. It can often take a matter of hours for the results of these tests to be communicated to the physician in charge of that patient. Accordingly, it is not uncommon for the physician to begin treating a patient without knowing the results of any requested testing.

In situations where the patient is seriously ill, the delay incurred in testing samples could conceivably put the well-being of that patient at risk.

One might consider that a suitable way to overcome this problem would be for the physician in charge of a particular patient to conduct the testing himself/herself, without sending the samples away to a laboratory. However, the testing of samples is often a complex process which must be carried out by highly skilled personnel if the results are to be reliable and hence of any real use to the physician.

Therefore, there is a need in the art for an apparatus which can be quickly and reliably operated by a user (who will sometimes be referred to as an operator) to test samples, particularly samples obtained from patients.

In accordance with the present invention, there is provided an automatic diagnostic apparatus comprising: a controller for controlling operation of the apparatus and for processing data; a sensing system operably connected to the controller for performing an assay, preferably an electrochemical assay (more preferably an electrochemical immunoassay), of a sample and communicating data from said assay to said controller: optionally voltage supply means for applying a potential difference to said sensing system-, and output means for communicating processed data to a user.

The present invention therefore provides an automated apparatus for the testing of samples, especially patient samples. If patient samples are tested then the results of this testing can be made available to a physician within a matter of minutes and thus provide an early and rapid diagnosis of a patient's condition.

In accordance with the present invention, there is also provided a method of automatic diagnosis, the method comprising the steps of:
(a) placing a sample within an automatic diagnostic apparatus;
(b) optionally generating instructions with a controller for instructing a voltage supply means to apply a voltage to a sensing system;
(c) controlling said sensing system with said controller to perform an assay, preferably an electrochemical assay (more preferably an electrochemical immunoassay), of said sample and to generate data for output to said controller;
(d) processing said data in said controller to generate processed data; and
(e) outputting said processed data to a user.

The automatic diagnostic apparatus, and the method of operating the same, is particularly useful for the testing of acute myocardial infarction and for the monitoring of reperfusion.

Accordingly, in accordance with a preferred embodiment of the present invention there is provided a method of automatically diagnosing myocardial infarction, the method comprising the steps of: monitoring ex vivo levels of one or more detectable cardiac marker proteins, such as any one or more of CK, CK-MM, CK-MB, myoglobin, cardiac myosin light chain(s), Troponin T or Troponin 1, or a cardiac marker suitable for the diagnosis of acute myocardial infarction. Advantageously, this method enables a quantitative assay to be conducted for these protein combinations.

Preferably the above method is accomplished with the above mentioned apparatus.

However, it will of course be understood, that whilst the present invention is preferably used for diagnostic testing for myocardial infarction, other testing (such as for any other clinical condition) may alternatively be conducted. Thus, the present disclosure is not to be read as being limited to the diagnostic testing of myocardial infarction only.

Prior to the testing of a patient's condition, it is often necessary to separate the sample from the patient into its constituent components. This separation is usually accomplished by placing the sample in a test tube, for example, and spinning the test tube at high speed in a centrifuge.

Throughout the spinning process, the sample separates into its constituent components with the heavier components moving towards the bottom of the test tube and the lighter components moving towards the top of the test tube. For example, if a sample of blood is taken and spun as described above, the heavier red blood cells move towards the bottom of the tube and the lighter plasma moves towards the top of the test tube.

The required portion of the sample may then be removed from the test tube. However, the operator must be careful to ensure that the tube is not subject to any further agitation, as such agitation may cause the components to recombine. The operator must also be careful to ensure that when he/she withdraws the required component of the sample, that component is not contaminated with any of the other component in the tube. Thus the withdrawing of separated components from a spun sample can be problematic.

In accordance with the present invention, there is also provided a container having a first base and a second base, said second base being raised from said first base and having a depression provided therein, such that when material comprising a heavier component and a lighter component is placed within said container and spun, said heavier component is forced towards said first base and said lighter component is forced towards and onto said second base and subsequently retained within said depression.

In this way, the lighter component of a separated material may be easily withdrawn from the depression by an operator (which may be a mechanical or an electromechanical operator). Furthermore, the risk of that operator accidentally contaminating the lighter component with the heavier component, either by agitating the container or accidentally withdrawing any of the heavier component, is significantly reduced.

United Kingdom Patent Application No. 9409449.7 (published as GB-A-2 289 339) discloses an electrochemical through-flow immunoassay biosensor. The biosensor comprises a solid phase immunoassay system, a porous working electrode, a counter electrode and a means for producing a fluid flow through the biosensor. Whilst this arrangement produces excellent results in the laboratory, it could suffer from a number of drawbacks when used in a clinical environment requiring rapid analysis of a number of samples. The most significant of these may be associated with the fact that the biosensor must be thoroughly cleaned before it can be used again, or used to test another sample. Conceivably, the biosensor could be thrown away immediately after use. However, the relatively expensive material from which the preferred biosensor body and preferred biosensor electrodes are manufactured could quickly make such a strategy uneconomic. In addition, the associated equipment used with the biosensor would still have to be thoroughly cleaned and so, any time saving attained by the disposal of the biosensor would be counteracted by the time needed to clean the associated equipment.

In accordance with the present invention, there is also provided a disposable electrochemical immunoassay biosensor comprising: a sensor body with a depression therein and a sensor outlet in said depression, an apertured counter electrode provided in abutment with one side of said depression such that said counter electrode aperture communicates with said outlet: an apertured working electrode provided in abutment with another side of said depression such that said working electrode aperture communicates with said sensor outlet, an immunoassay system provided in close proximity to said working electrode, and an apertured sensor inlet means also provided within said working electrode and in communication with said immunoassay system, wherein said sensor body is manufactured from a plastics material and said working and counter electrodes are manufactured from an electrically conductive plastics material.

Preferably, the immunoassay system is provided within the working electrode.

Alternatively or additionally, at least one of the electrodes may include other conventional electrode materials, such as silver (Ag)/silver chloride (AgCl).

In this way, the biosensor of the present Invention may be manufactured from relatively inexpensive materials and, thus, a new biosensor may be used for each test and the old biosensor may be disposed of. The use of such a biosensor removes the need for extensive time-consuming cleaning of the biosensor.

In accordance with another embodiment of the invention, there is also provided a conducting plastic electrode suitable for use in a diagnostic apparatus. The present invention also provides for use of a conducting plastic electrode for an electrochemical immunoassay.

In order to perform an electrochemical immunoassay with conventional techniques, the operator would first have to prepare a suitable reagent. The preparation of this reagent may be a relatively complex process that would probably have to be repeated on each occasion that a diagnostic test was to be undertaken. By way of example, for a physician operating in his/her surgery, the preparation of suitable reagents would require the physician to keep stocks of necessary chemicals and to waste valuable time making up suitable reagents.

Furthermore, each preparation of a suitable reagent by the physician may be subject to minor variations that could cause doubt to be cast on tests made on the same patient, but with different sets of reagents.

Also, if a physician were to prepare a number of different reagents for use with different diagnostic tests, it is conceivable that these reagents could become contaminated with each other or, more seriously, one reagent could be mistaken for another.

Thus, there is a need in the art for a suitable means for an operator, such as a physician, to prepare consistent reagents without having to waste time and without having to maintain a large stock of chemicals. The means must also enable the physician to tell quickly and easily one reagent from another.

In accordance with the present invention, there is provided a disposable reagent cartridge comprising a body with at least one depression therein; and a removable cover sealed over said depression; wherein at least a reagent (which may be the same or different) is provided within each of said at least one depression and said removable cover is provided with a bar-code on an outer side thereof, said bar-code being usable to identify said reagent(s) and/or a diagnostic test requiring said reagent(s).

As mentioned above the present invention may be used for the monitoring and the diagnosis of acute myocardial infarction. Accordingly, the present invention provides a disposable reagent cartridge for diagnostic testing of myocardial infarction, the cartridge comprising a plastic body with four depressions therein and a removable cover sealed over said depressions; wherein a first depression is filled with a buffer solution, a second depression is filled with a wash solution, a third depression is filled with dried naphthyl phosphate, a fourth depression is filled with dried enzyme substrate (which may be alkaline phosphatase) (preferably associated with an antibody, more preferably an antibody for an antigen associated with a clinical condition—such as acute myocardial infarction) and said removable cover is printed with a bar-code on an outer side thereof, said bar-code being usable to identify said contents within one or more of the depressions (reagents) and/or the diagnostic test.

In accordance with the present invention, there is also provided prepacked disposable diagnostic testing kit sealed with a removable cover, the kit comprising at least one disposable sample holding means, at least one disposable electrochemical biosensor, at least one disposable through-flow producing means and at least one disposable reagent cartridge, wherein said each of said at least one disposable reagent cartridge is prepacked with at least one reagent for the performance of at least one diagnostic test and then sealed with a removable seal.

In order to perform a diagnostic test, the operator (e.g. physician) need only tear off a removable cover from the kit and operate the contents thereof to perform the test. As the test may be performed with only the contents of the kit, the operator does not have to waste time cleaning any other pieces of equipment.

Embodiments of the present invention will now be described, by way of example only, with reference to the accompanying drawings, in which like numerals represent like parts, and in which.

Figure 5:
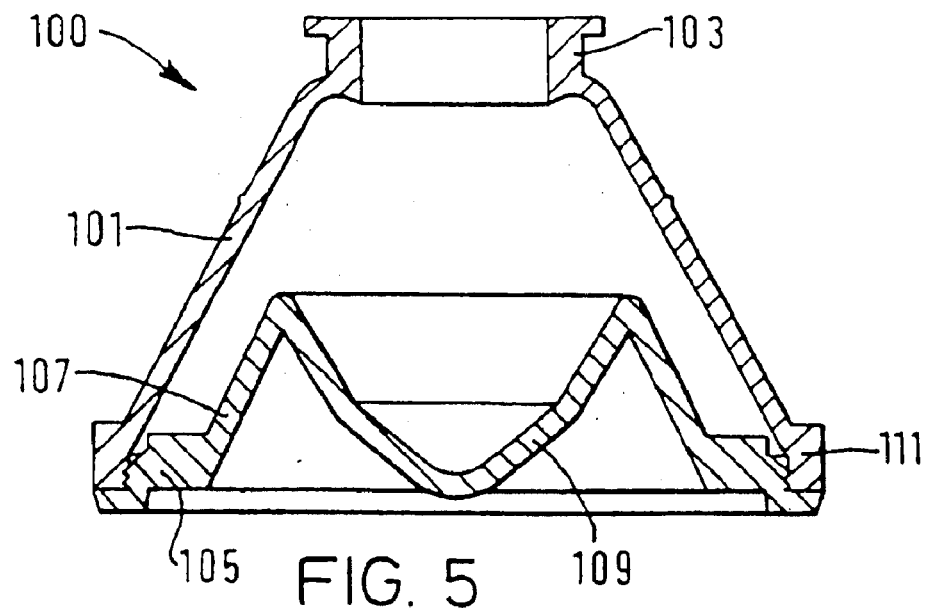
FIG. 5 is a schematic representation in cross-section of a container.
Figure 6:
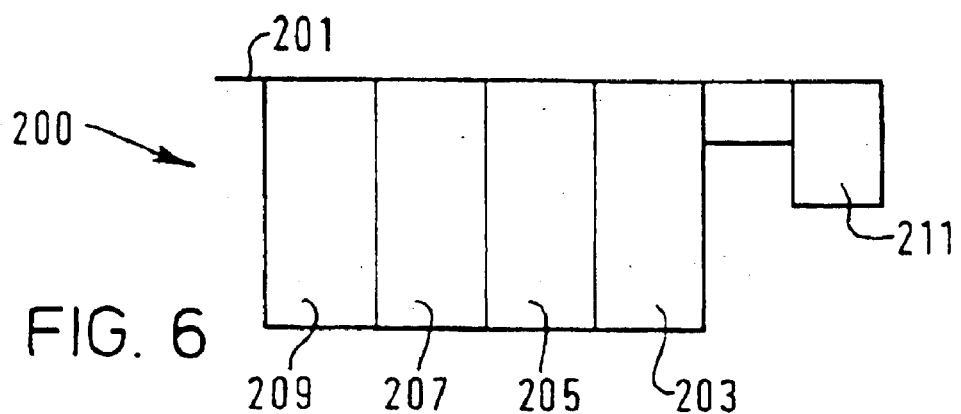
FIG. 6 is an elevation of a reagent cartridge.
Figure 11:
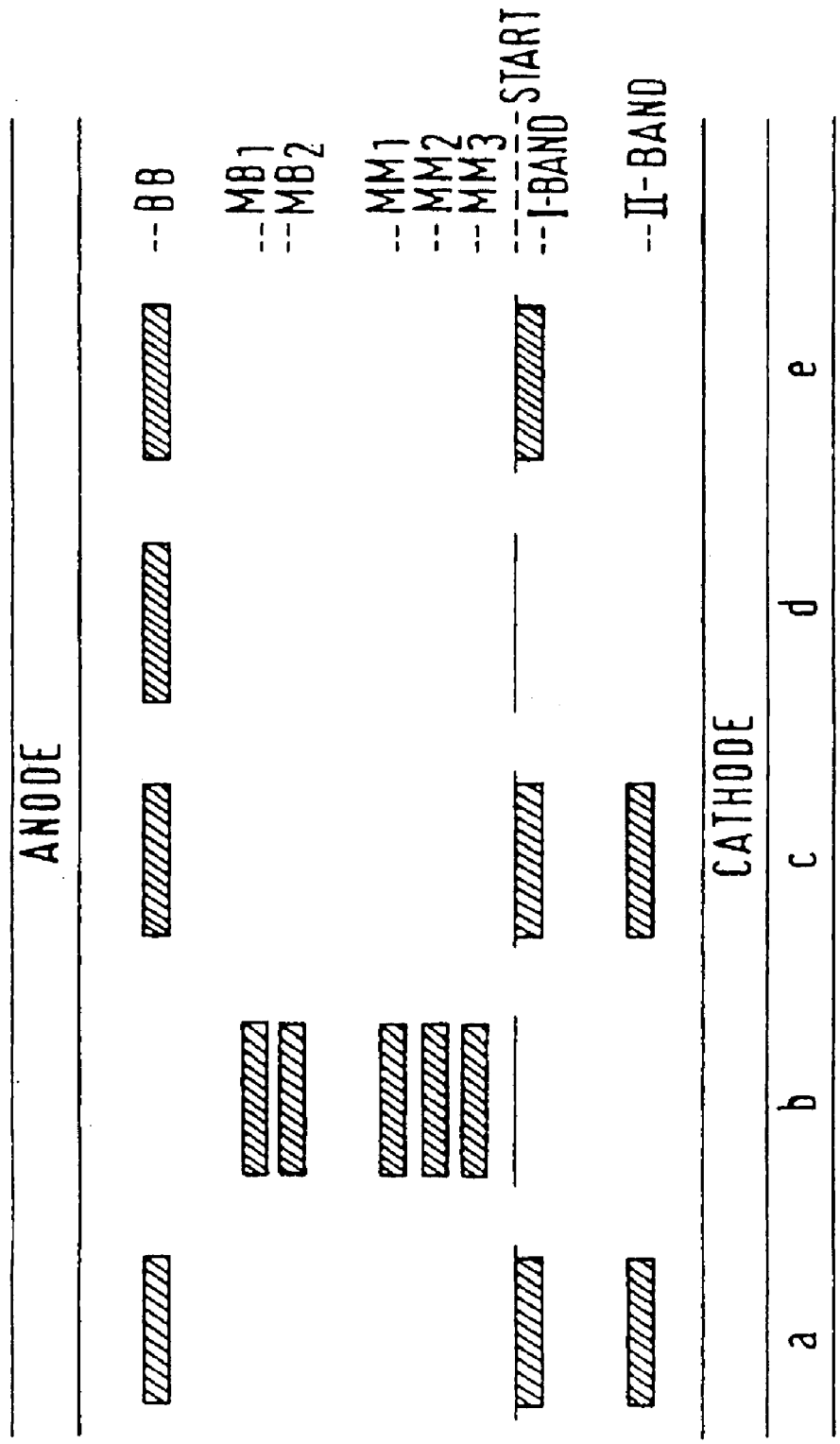
Figure 12:
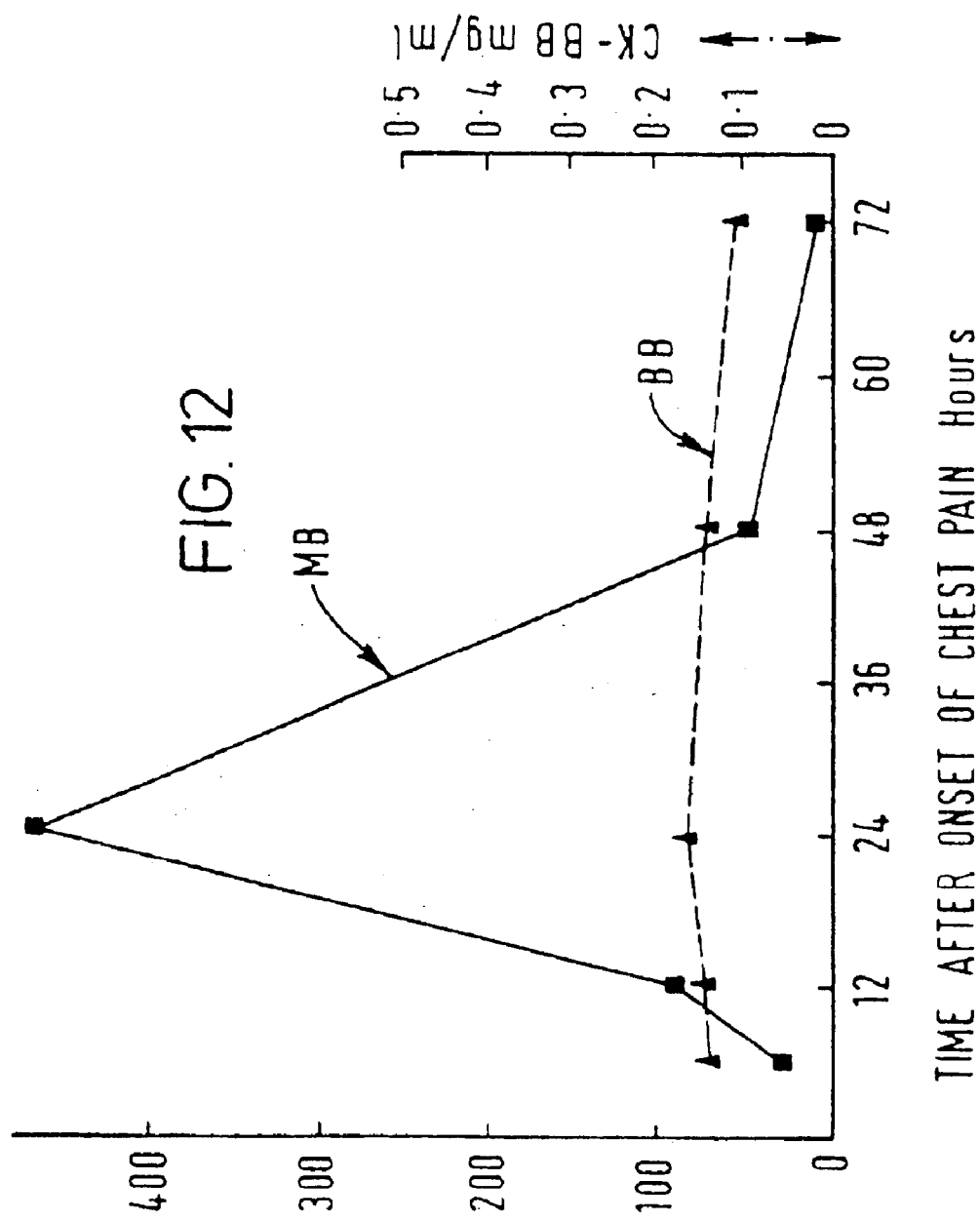
Figure 13A:
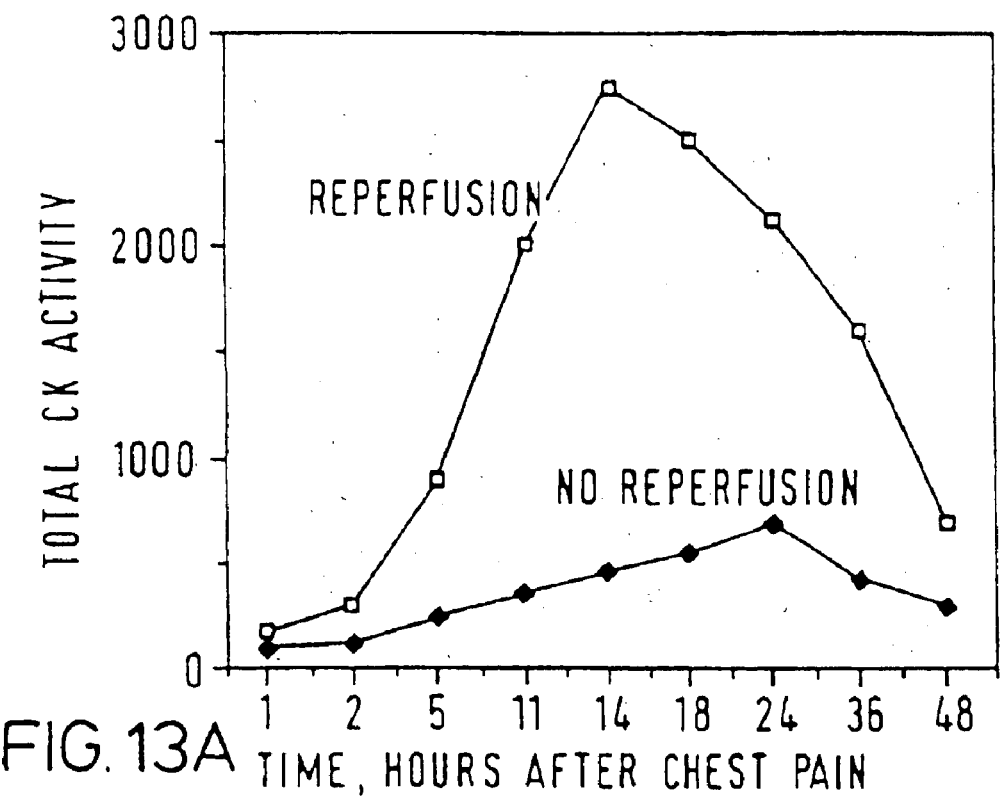
Figure 13B:
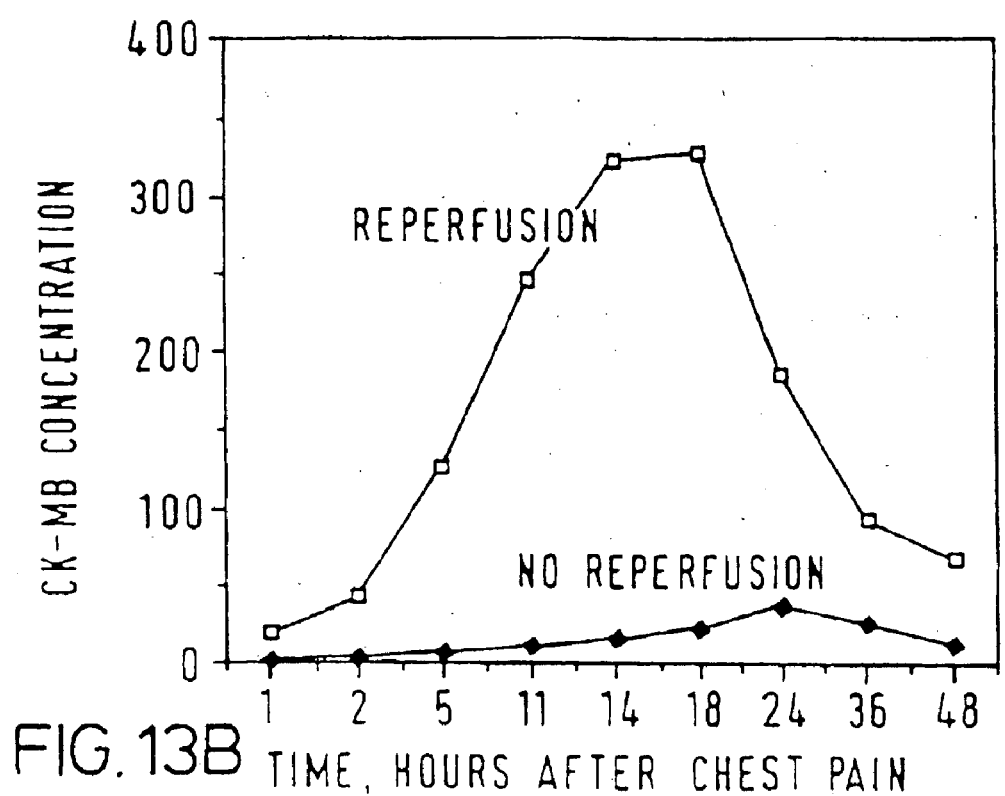

FIG. 11 is a series of electrophoretograms and is taken from FIG. 5 of "A Study on the Dimeric Structure of Creatine Kinase" by R. A. Wevers, H. P. Olthuis, J. C. C. van Niel, M. G. M van Wilgenburg and J. B. J. Soons, published in Clinica Chimica Acta, 75 (1977) pp 377–385;

FIG. 12 is a graph and is taken from FIG. 6 of "Two-Site Monoclonal Antibody Assays for Human Heart- and Brain-Type Creatine Kinase" by A. P. Jackson, K. Siddle and R. J. Thompson, published in Clinical Chemistry, Vol.30 No.7 (1984), pp 1157–1162; and FIGS. 13A and 13B present two graphs and is taken from FIG. 1 of "Acute Myocardial Infarction and Coronary Reperfusion" by F. S. Apple, published in Clinical Chemistry (Review Article), A.J.C.P. February 1992 Volume 92, No.2.

FIGS. 14 and 15 are graphs.

Figure 1:
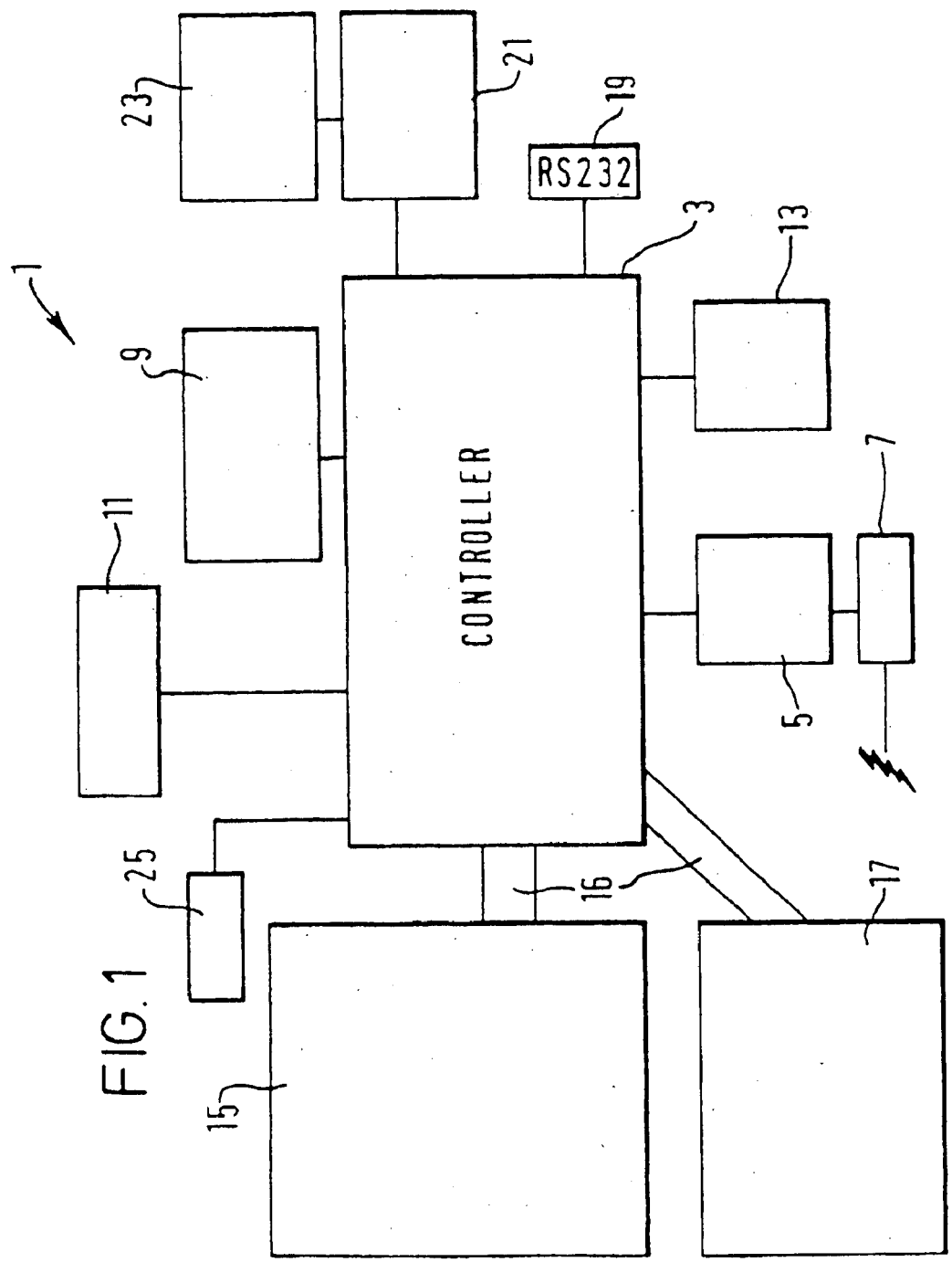
FIG. 1 is a schematic representation of an automatic diagnostic apparatus.

FIG. 1 shows a schematic representation of an automatic diagnostic apparatus 1. The apparatus 1 comprises a controller 3 for controlling operation of the apparatus and all of the components thereof. The apparatus 3 is powered from a power supply unit 5 which includes a transformer 7. A user input 9, in this case a 16-key keypad, enables a user to input instructions and data to the controller 3. Data and instructions for the user are displayed on a display 11. Also provided for the input of data into the controller 3 is a bar code scanner 13.

The controller is connected by ribbon cables 16 to a syringe and biosensor system 15 and a rack and platform system 17. It is these systems that manipulate samples taken from a patient and generate readings therefrom.

Also provided for the output of data to a user are an RS232 port 19 and a printer interface 21 which is in turn connected to a printer 23. The RS232 port 19 may be connected to a Personal Computer (PC) if desired.

The controller is also connected to a lid sensor 25 which senses whether the apparatus's lid is open or closed. The controller will not allow the apparatus to operate until the lid of the apparatus has been closed.

Figure 2:
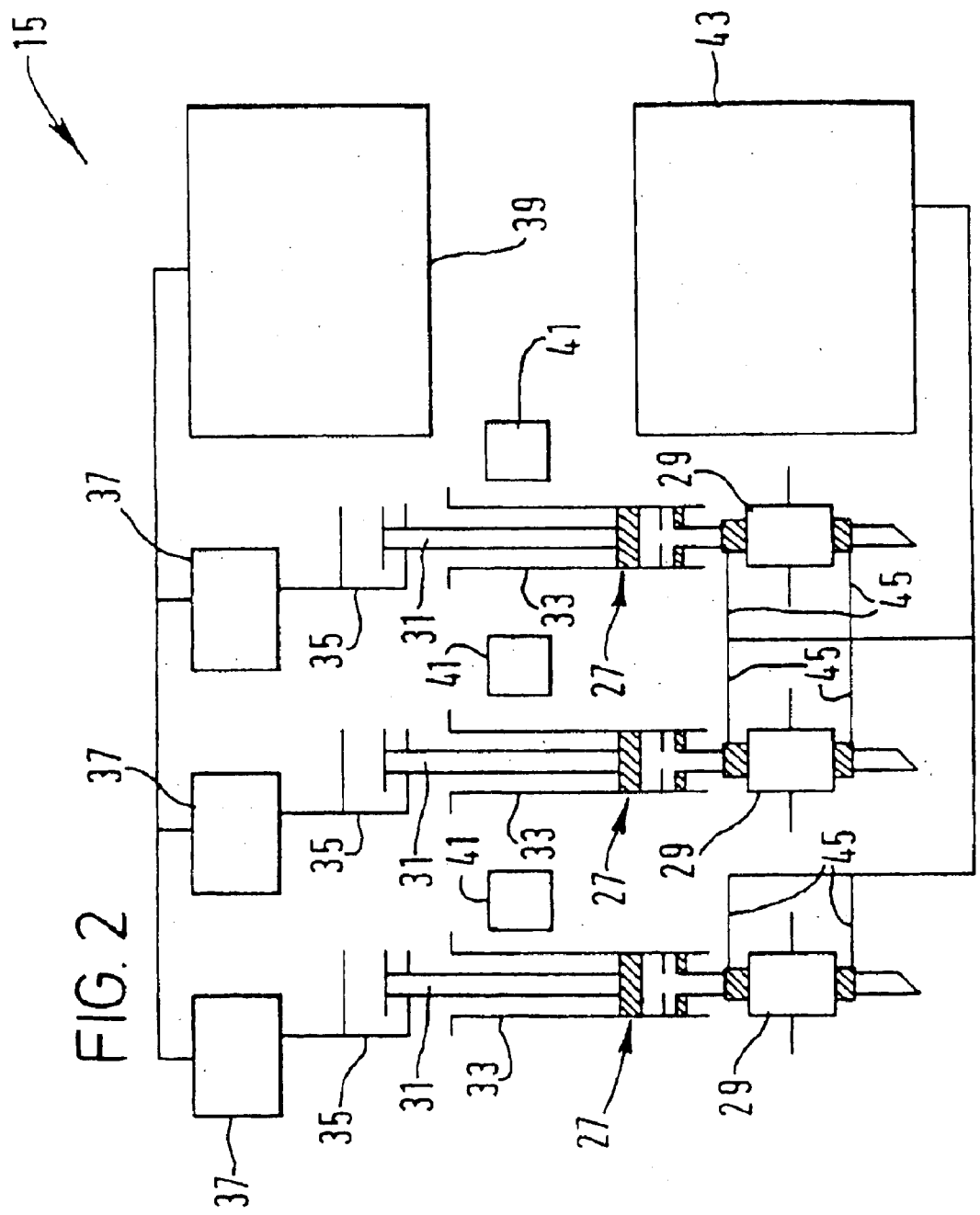
FIG. 2 is a schematic representation of a syringe and biosensor system as shown in FIG. 1.

FIG. 2 is a schematic representation of a syringe and biosensor system 15 as shown in FIG. 1. As shown, the system 15 comprises three sets of syringes 27 and associated biosensors 29. It will be appreciated, of course, that the number of sets may be varied at will. In one example, the system may be used as a means for diagnosing myocardial infarction by variations in three parameters. Tests for alternative ailments may require a fewer or greater number of sets.

The biosensors 29 are electrochemical immunoassay biosensors, and may be constructed from plastic material at a reduced unit cost. The reduced cost of these biosensors 29 enables them to be disposed of after each test without prohibitively increasing the cost of operating the apparatus. The construction of an example of the biosensor will be described later in conjunction with FIG. 8. Conventional electrochemical immunoassay biosensors could, of course, alternatively be provided.

The syringes 27 are, in this embodiment, simple commonplace syringes which comprise a plunger 31 and a syringe body 33, and are used to generate a fluid flow through the biosensors 29. It will be understood, that whilst syringes have been described, other flow-flow producing means may alternatively be provided. For example, a fluid flow could conceivably be generated by drawing fluid through the biosensors with a pump. The pump could be connected to each of the biosensors by a disposable pipe, for example, which could be discarded after a test has been conducted.

As shown in FIG. 2, one end of the plunger 31 is connected to an arm 35 of a biosensor motor 37. During use of the apparatus, the motor 37 may be operated by a biosensor motor control board 39 to move the arm 35 and attached plunger 31 in and out of the syringe body 33 thereby to generate a flow through a biosensor 29 attached to an opposite apertured end of the syringe body 33. The biosensor motor control board 39 is in turn controlled by the controller 3. Three syringe sensors 41 are provided that enable the controller 3 to sense whether a syringe 27 and attached biosensor 29 has been correctly placed in the apparatus before the testing is commenced.

A biosensor control board 43 under control of the controller 3 is provided. The board 43 is provided with contacts 45 for each biosensor 29 of the apparatus and is operable under instruction of the controller 3 to apply a voltage to each biosensor 29 as required. The biosensor control board 43 measures a current flowing through each biosensor 29, digitizes the data and outputs it to the controller 3. In common with other through-flow immunoassay biosensors, the current through the biosensor is indicative of the quantity of material-to-be-sensed in a sample under test. In this embodiment, the controller 3 is an EPROM microcontroller with a 32 KB (kilobyte) ROM (Read Only Memory) and a 32 KB (kilobyte) RAM (Random Access Memory), although other arrangements are conceivable.

Figure 3:
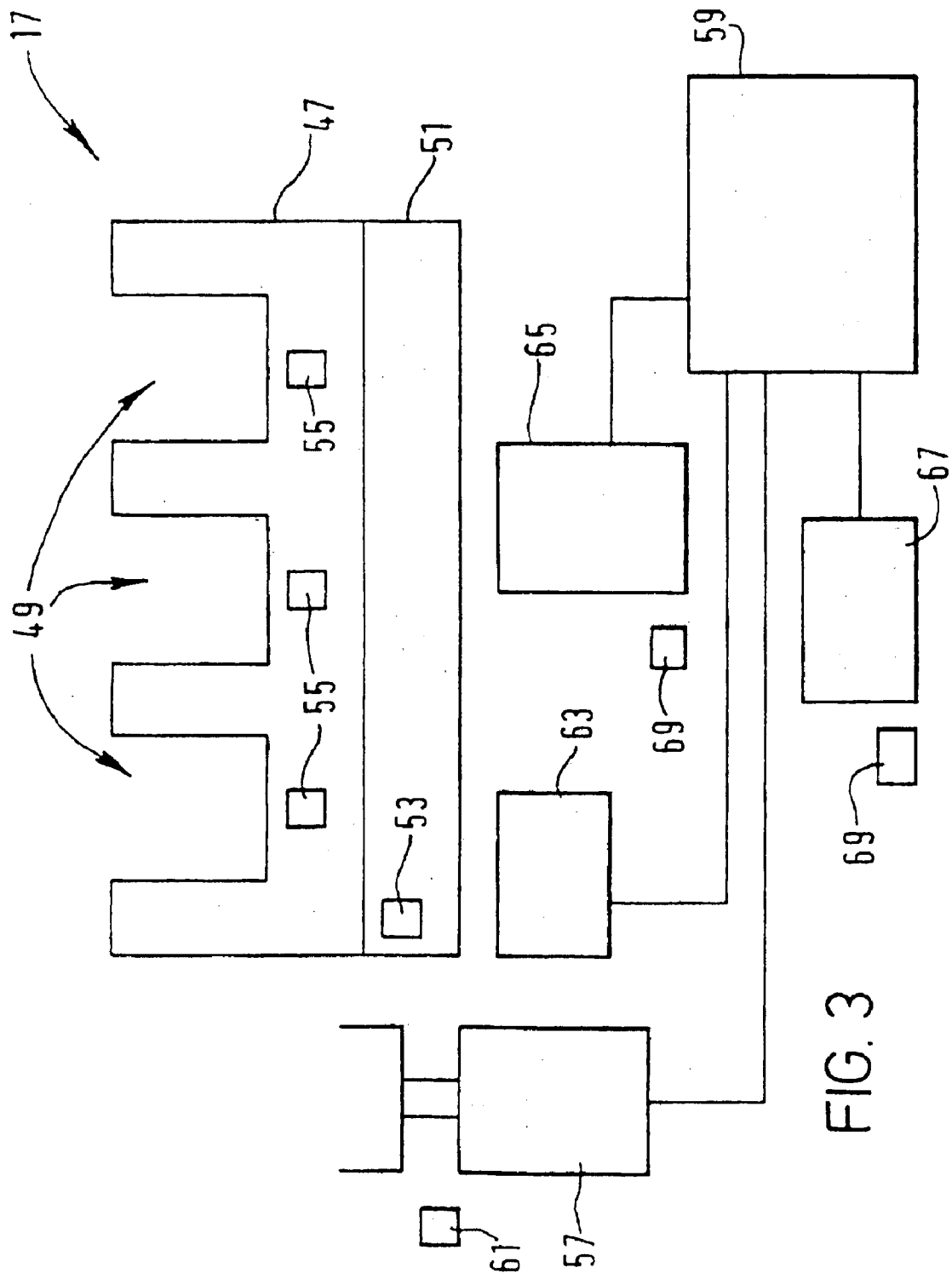
FIG. 3 is a schematic representation of a rack and platform system also as shown in FIG. 1.

FIG. 3 is a schematic representation of a rack and platform system 17 also as shown in FIG. 1. The rack and platform system comprises a block 47 with three shaped apertures 49, each for securely holding a reagent cartridge (not shown). A suitable reagent cartridge will be later described in relation to FIGS. 6 and 7. The block also includes an electrical heater 51 which may be used as required to heat the cartridges in the rack and platform system 17. The block 47 is provided with a heat sensor 53 which relays temperature data to the controller 3, which responds by switching on or switching off the heater 51 as required.

Whilst the apparatus of FIG. 3 illustrates three apertures for holding three cartridges, it will be appreciated that a greater or lesser number of apertures and cartridges may alternatively be provided. In each of the apertures 49, a cartridge sensor 55, under control of the controller 3, is provided that senses whether a cartridge has been correctly placed in the aperture 49. If a cartridge is missing from one of the apertures 49, the controller 3 senses the absence of that cartridge and will not generate any data for the sensing system associated with that cartridge position.

Also provided is a rotor motor 57 which is operable to spin a sample container (100) placed in operable communication therewith. A suitable sample container is later described in relation to FIG. 5. The rotor motor 57 is under the control of a motor control board 59 which is in turn controlled by the controller 3. The rack and platform system 17 is provided with a rotor sensor 61 which senses whether a sample container has been correctly placed in communication with the rotor motor 57 and communicates this information to the controller 3. The motor control board 59 also controls a rotor index motor 63 which is operable to align the rotor motor 57 and attached sample container with each sensing system of the apparatus.

The rack and platform system 17 is also provided with an up/down motor 65 and a forward/back motor 67 for moving the rack and platform System 17 in any of the aforementioned directions. The up/down and forward/back motors are controlled by the motor control board 59 in the rack and platform system 17. A pair of home sensors 69 are provided which sense when the block 47 is at it's "home" position in the forward/back and/or up/down directions. The "home" position is when the block 47 is at its furthest point from the sensing system in a forward/back and up/down direction. The home sensors 69 communicate position data to the controller 3.

At this juncture, it is appropriate to provide a brief general description of the manner in which the apparatus operates and is operated. Typically, a user decides, as a first step, which test they wish to perform for a particular patient. An appropriate diagnostic kit is selected and the various components removed therefrom. Next, a bar-code on the reagent cartridge (or any other part of the kit) is read with the bar-code scanner 13 and the cartridge is placed in the block aperture 49. In accordance with the bar-code, the controller 3 displays on the display 11 the type of test to be conducted and sets up the apparatus vis-a-vis the number of reagent compartments required and the testing routine to be undertaken. The user may then visually inspect the display 11 to check that they are indeed about to conduct the desired test.

Next, the user takes a fluid sample from a patient and places the sample in a container provided in the kit. The container is then placed in operable communication with the rotor motor 57 in the rack and platform system 17. The rack and platform system 17 is, at this stage, at its "home" position—i.e. at its furthest position from the sensing system 15—so as to improve user accessibility to the apparatus.

It will be apparent that bar-codes may also be provided on any of the biosensor, container and syringe.

Next, the user takes a biosensor 29 and a syringe 27 from the kit, and fits them together (alternatively, the biosensor and syringe may be supplied pre-fitted together). The connected biosensor 29 and syringe 27 are then placed in the sensing system 15 with one end of the syringe's plunger 31 in communication with the biosensor system motor arm 35. The other end of the plunger 31 internally abuts the syringe's base. The biosensor 29 is fitted within the sensing system 15 in such a manner that the sensing system contacts 45 electrically connect with electrodes in the biosensor 29. The apparatus is now primed and ready for testing the sample.

The controller 3, via the various sensors, senses that the container, cartridge, biosensor and syringe have been correctly placed in the apparatus and waits until the closing of the apparatus lid has been sensed by the lid sensor 25. When the lid has been closed the controller 3 begins the testing process.

Firstly, the controller 3 instructs the rack and platform system motor control board 59 to operate the forward/back motor 67 so that the block 47 is withdrawn into the apparatus in such a fashion that each cartridge container is positioned below each biosensor 29.

Next, the controller 3 instructs the rack and platform system motor control board 59 to operate the rotor motor 57 and so to spin the container placed in communication therewith. The centrifuging of the sample in the container continues at approximately 400 revolutions per minute for some four minutes until the sample is properly separated (other rotational speeds may be adopted if desired). Whilst the sample is being spun, the controller 3 instructs the rack and platform system motor control board 59 to move the block 47 towards the biosensor 29 until the tip of the biosensor protrudes into a compartment of the reagent cartridge.

If the reagents need to be made up from constituents in the reagent cartridge, the controller 3 may then instruct the sensing system motor control board 39 to operate the biosensor motor 37 to move the attached syringe plunger 31 in and out of the syringe body 33 thereby to draw fluid into and to expel fluid from the biosensor 29. In addition, the controller 3 may simultaneously instruct the rack and platform system motor control board 59 to move the block 47 and hence the reagent cartridge up, down, forward or back so that reagents may be mixed between compartments of the reagent cartridge until a final desired reagent is achieved.

Optionally, the controller 3 may then instruct the biosensor motor 37 to withdraw the plunger 31 from the syringe body 33 and draw an amount of reagent provided in the reagent cartridge through the biosensor 29. Simultaneously, the controller 3 may instruct the biosensor control board 43 to apply a voltage to the biosensor 29 and measure the current flowing in the biosensor 29. If the current is below a predetermined threshold, the controller 3 determines that the integrity of the reagent has been maintained. If, however, the current is above the threshold, then the controller determines that the integrity of the reagent has been compromised and the apparatus is halted and a suitable message displayed to the user requesting the user to replace the reagent cartridge with another reagent cartridge. The example later described below will exhibit such a step.

Next, the controller 3 instructs the rack and platform motor control board 59 to move the sample container so that the container is directly below the biosensor 29. The controller 3 then instructs the rack and platform motor control board 59 to move the container so that the biosensor 29 dips into a lighter portion of the separated sample. The controller 3 then instructs the biosensor motor 37 via the biosensor motor control board 39 to move the plunger 31 and draw a quantity of separated sample into the biosensor 29. The controller 3 then instructs the rack and platform motor control board 59 to cause the movement of the cartridge until the cartridge is directly below the biosensor 29 and the biosensor 29 dips into the reagent in the reagent cartridge. The controller 3 then instructs the biosensor motor control board 39 to move the plunger 31 and draw a quantity of reagent (which may be rehydrated substrate) through the biosensor 29. As an additional step, the controller 3 may then instruct the rack and platform motor control board 39 to cause the cartridge to be moved again so that the biosensor 29 once more dips into the cartridge and a wash solution is drawn through the biosensor 29 to wash any excess reagent from the biosensor 29.

Then the controller 3 instructs the biosensor control board 43 to apply a voltage to the biosensor 29 and to measure the produced current. The current value is then communicated to the controller 3 as testing data via the ribbon cable 16.

The controller 3 then processes the testing data and outputs the processed data to the user. The controller may also store the data so that a plurality of results may be stored over time for a particular patient. The results may then be outputted to the user in the form of a graph via the printer 23.

One example of data collection and processing will now be described. The current flowing through the sensor is recorded at precise intervals. The typical current response after applying the potential to the sensor is a decay curve. When the substrate reaches the sensor the decay quickly becomes an exponential growth curve to a peak plateau. Typically, a quantity of electrical charge is estimated initially, which is taken as the area between the two curves the lower curve being interpolated beneath the growth curve by examination of the decay rate. The turning point where decay becomes growth is called the start of peak and is determined by software in the controller by looking for a trend when the average rate of change over a number of samples reaches a threshold value. The assay result required is the concentration of analyte which is obtained by the formula:

$$conc = \frac{charge - b}{a}$$

where a and b are parameters read from the bar code or database.

Figure 4:
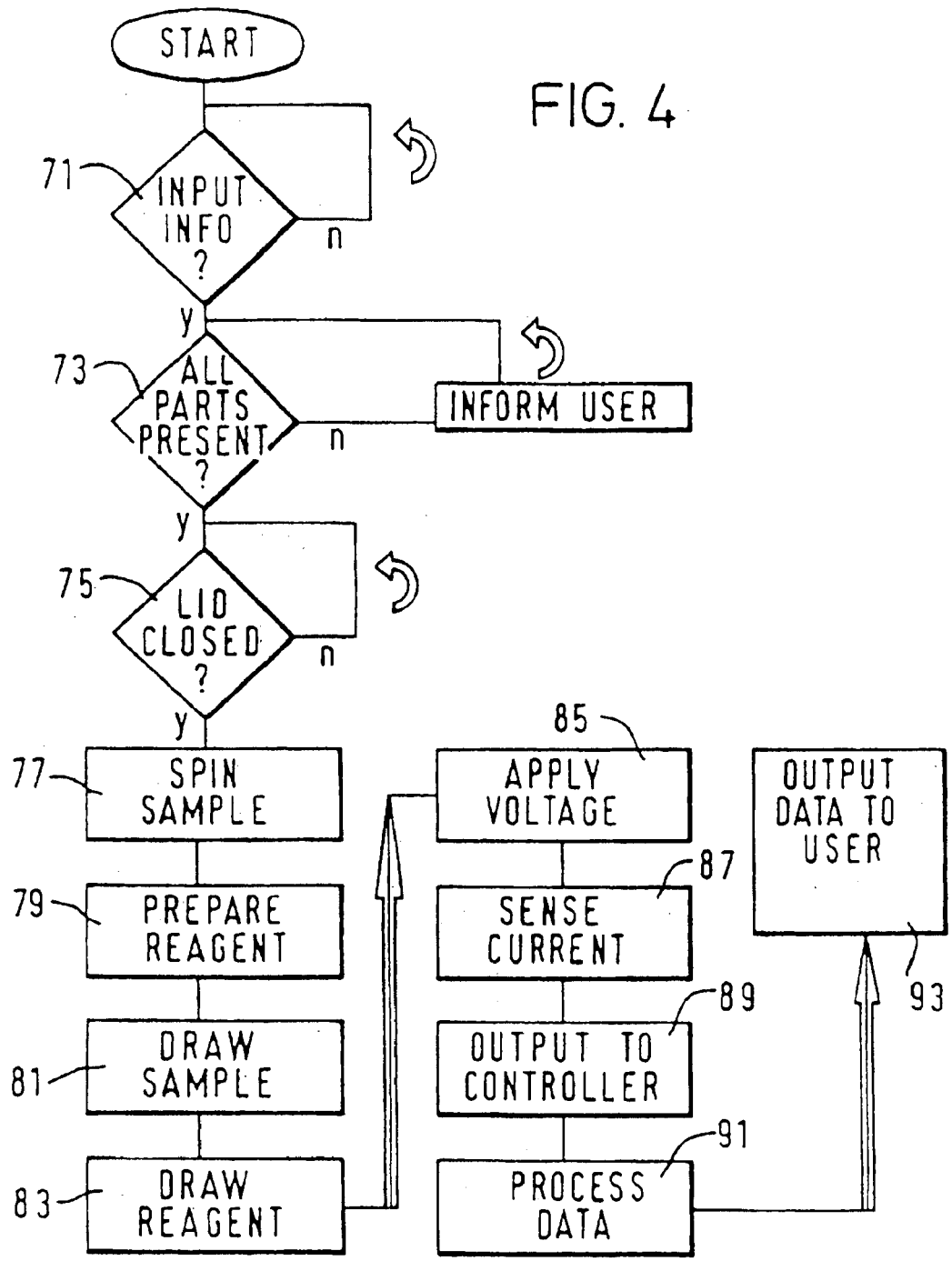
FIG. 4 is a flow diagram generally illustrating the operation of the apparatus depicted in FIGS. 1, 2 and 3 under control of a controller.

FIG. 4 is a flow diagram generally illustrating the operation of the apparatus depicted in FIGS. 1, 2 and 3 under control of a controller. With reference to FIG. 4, the stages undertaken by the apparatus are as follows.

In a first step 71, the controller 3 waits for the input of bar-code information or the input of keypad information regarding the test to be undertaken. In a second step 73, the controller 3 uses the connected sensors to sense whether the container, cartridge, syringe and biosensor have been correctly placed in the apparatus. If so, then in a third step 75, the controller 3 uses the lid sensor 25 to sense whether the lid is open or closed. If the lid is closed, then the controller, in a fourth step 77, causes the spinning of the sample in the container. The controller 3, in a fifth step 79, then prepares the reagent(s) in accordance with the inputted bar-code or keypad information. In a sixth step 81, the controller 3 instructs the apparatus to draw separated sample through the biosensor 29 and then, in a seventh step 83, instructs the apparatus to draw the reagent(s) through the biosensor 29. In an eighth step 85, the controller 3 instructs the apparatus to apply a voltage to the biosensor 29 and, in a ninth step 87, to measure the current flowing in the biosensor 29. In a tenth step 89, the sensed current data is digitised and outputted to the controller 3 for processing in an eleventh step 91. In a final twelfth step 93, the processed data is outputted to the user.

As mentioned above, the apparatus may be used to diagnose myocardial infarction by testing three blood parameters. In such an example, the reagent cartridge would contain the following reagents in four separate compartments. The first, largest compartment would contain a buffer solution. The second compartment, smaller than the first compartment, would contain a wash solution. The third compartment, smaller than the second compartment, would contain a dried substrate (which in one example may be naphthyl phosphate). The fourth compartment, smaller than the second compartment, would contain a conjugate (which in one example may be the enzyme Alkaline Phosphatase (ALP), preferably associated with an antibody, more preferably an antibody for an antigen associated with a clinical condition—such as acute myocardial infarction).

When using such a cartridge, the buffer solution would be used to rehydrate the dried substrate and the integrity of the substrate would then be checked by way of the biosensor 29 in the above described manner. The wash solution would be used to remove any excess conjugate from the biosensor 29. In this example, the controller 3 would instruct the apparatus to perform the above mentioned additional step of testing the integrity of the rehydrated substrate by passing rehydrated substrate through the biosensor 29 whilst applying a voltage thereto. If the detected current is less than substantially 80 nA (nanoamperes), the controller 3 determines that the substrate integrity is maintained. A current level above this threshold causes the controller 3 to determine that the substrate integrity has been compromised.

The biological processes being undertaken in the biosensor have already been described in United Kingdom Patent Publication No. 2 289 339 mentioned above, and so will not be described in any great detail herein. However, to further illuminate the operation of the present invention, a brief summary will now be given.

FIG. 5 is a schematic representation in cross-section of a container 100. The container 100 comprises a substantially frusto-conical outer wall 101, with a lip 103 at its narrow end. The outer wall 101 connects at its broader end with a substantially planar annular first base 105. A second substantially conical inner wall 107 connects at its broader end with an inner edge of the annular first base 105. The inner wall 107 connects at its narrow end with a depression 109. The annular first base 105 is provided with a lip 111 on its outer edge to enable better communication of the rotor motor 57 with the container 100.

Prior to use of the apparatus, a sample of patient fluid is placed within the container 100 and the container is placed in communication with the rotor motor 57, thus forming a centrifuge (57, 100). Operation of the rotor motor 57 causes the container 100 to be spun about a central axis of the outer wall 101. Spinning of the container 100 causes heavier components of patient fluid to move towards the first base 105 and lighter components to move up the inner wall 107 to the second base 113 and to the depression 109 therein. The lighter components are then contained within the depression 109 for facilitated removal thereof.

It will be apparent that the external configuration of the above mentioned container 100 is not essential for the function which the container 100 is to perform, namely the separation of fluid components. It is the provision of a raised depression 109 that eases the separation of fluid components when centrifuged. Thus, the container herein described is not to be read as being limited by its external configuration or shape.

FIG. 6 is an elevation of a reagent cartridge 200. As shown, the reagent cartridge comprises a substantially planar body 201 with four reagent compartments (203,205,207, 209) depending therefrom. The reagent compartments are open at the surface of the planar body 201. At one end of the cartridge, there is provided a tube 211 sized so as to accept an inlet of a biosensor therein. In this way, the reagent cartridge and the biosensor may be fitted together so that they occupy a smaller volume when packaged prior to use.

Figure 7:
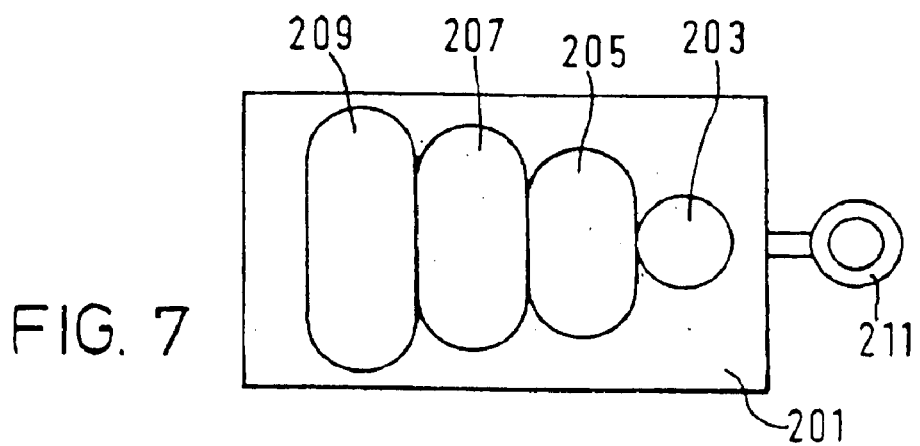
FIG. 7 is a plan view of the reagent cartridge of FIG. 6.

FIG. 7 illustrates a top plan view of the cartridge depicted in FIG. 6. As shown, the four reagent compartments are open at the planar body 201 and increase in volume from a smallest compartment 203 to a largest compartment 209. Of course, the size of the compartments may be varied at will. One end of the rube 211 is also shown in FIG. 7. The first compartment 203 has an approximately circular cross section and the second 205, third 207 and fourth 209 compartments have substantially elliptical cross-sections of increasing focal spacing.

The cartridge 200 of FIGS. 6 and 7 is initially filled with reagents for a particular diagnostic test that is to be undertaken. An example of a set of reagents for the testing of myocardial infarction (see earlier and later discussions). Once the compartments have been filled with reagent, then the cartridge 200 is sealed. Sealing of the cartridge 200 may be accomplished by adhering a removable metal foil cover to the planar body 201.

The cartridge 200 may thus be sealed and transported with a reduced risk of reagents becoming contaminated with each other, and with a reduced risk of reagents becoming spoiled. Immediately prior to use, the user can remove the cover to reveal the compartments and reagents. Alternatively, the reagent cartridge cover may be left in place and the biosensor tip may be arranged to pierce the cover where appropriate prior to removal of the cartridge contents. In either case, the user is provided with a set of reagents for a particular test without having to waste time preparing those reagents.

The cover (not shown) of the cartridge 200 may be provided with a bar-code. The bar-code gives information regarding the reagents contained within the cartridge 200 and may give information regarding the type of testing to be conducted with that cartridge 200.

As mentioned above, the apparatus of the present invention may be used for the diagnosis of myocardial infarction by electrochemical immunoassay. In this case, the cartridge 200 of FIG. 6 and FIG. 7 could be provided with the following reagents, for example. The first compartment 203 would be filled with a conjugate (which may be the enzyme ALP), the second compartment 205 would be filled with a dried substrate (which may be naphthyl phosphate), the third compartment 207 would be filled with a wash solution and the fourth compartment 209 would be filled with a buffer solution. In use, buffer solution would be taken from the fourth compartment 209 and added to the dried substrate to reconstitute the substrate solution. Other enzyme-substrate pairs are mentioned below.

Figure 8:
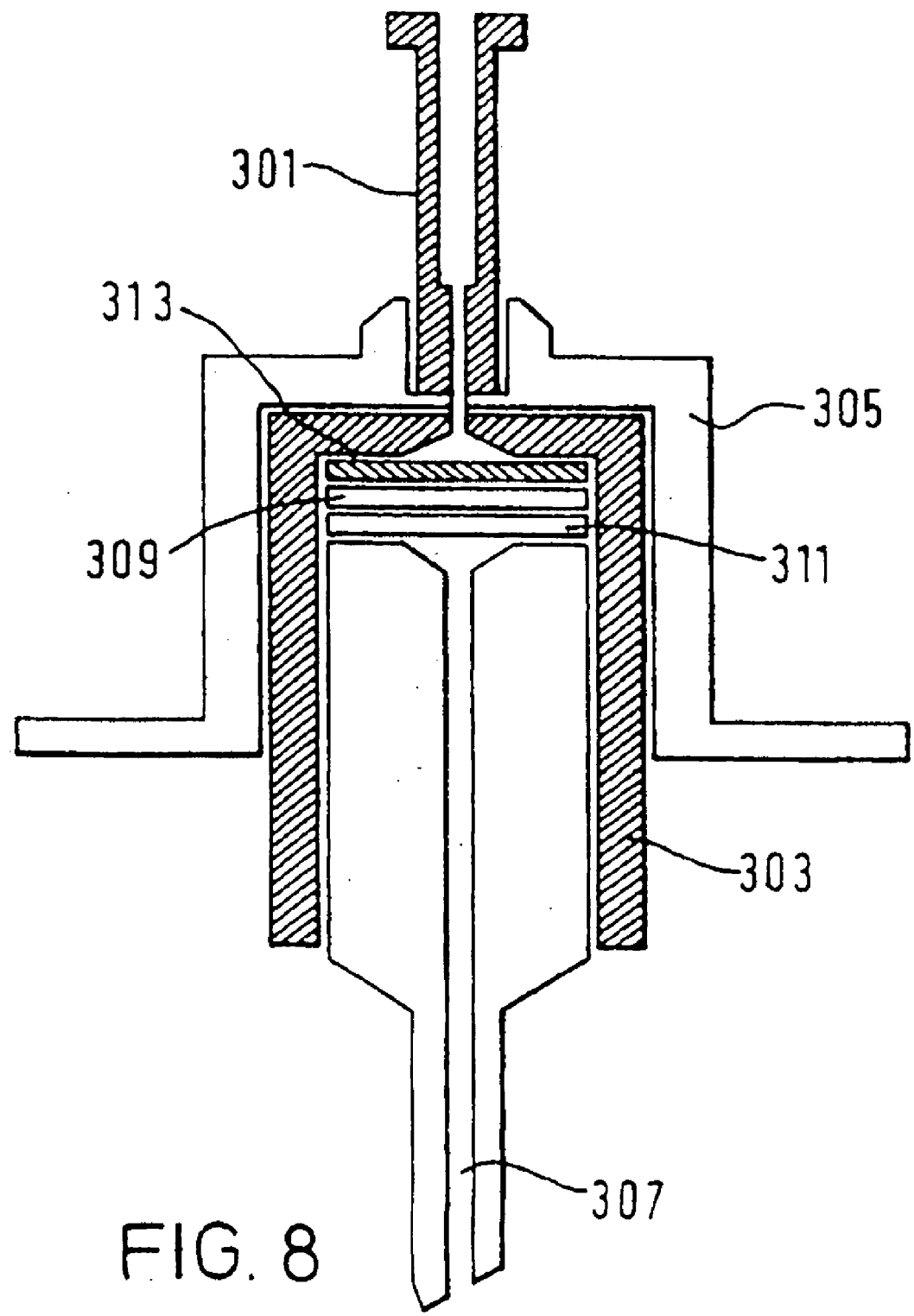
FIG. 8 is a schematic representation in cross-section of an electrochemical biosensor.

FIG. 8 is a schematic representation in cross-section of an electrochemical biosensor. With reference to FIG. 8, the biosensor comprises a counter electrode 301, a working electrode contact 303, a biosensor body, a biosensor inlet 307 and a solid phase immunoassay site comprising a porous spacer disk 309, a porous PVDF disk 311 and a porous graphite disk 313 as a working electrode. The spacer disk may be a Loprosorb™ disk, for example, and the graphite disk may be a Toray™ disk (Toray Industries, Japan).

As mentioned above, the biosensor may be used for conducting an immunoassay by testing parameters of a patient's blood sample. In an example of such a test, plasma is first separated from the patient sample—preferably by use of the container of the present invention—and then drawn into the biosensor by way of a syringe attached to the counter electrode 301. As the plasma passes from the biosensor inlet 307 through the biosensor, it traverses the porous PVDF disk 311. The porous PVDF disk 311 is impregnated with a particular antibody and the drawing of plasma through the disk causes the capture of an antigen under test on the disk 311.

Next, the syringe is used to draw a quantity of tracer antibody (preferably an antibody for an antigen associated with a clinical condition—such as acute myocardial infarction) conjugated to alkaline phosphatase (ALP) through the biosensor. As the conjugate passes through the PVDF disk 311, the antibody marks the antigen captured on the disk 311.

Next, the syringe draws up a quantity of wash solution which is used to wash any excess conjugate from the biosensor. Next, the syringe draws up a quantity of rehydrated substrate and a potential difference is then applied to the counter and working electrodes 301, 313 and a current is produced that is indicative of the quantity of antigen captured on the disk 311.

This process functions due to the electrochemical nature of the ALP and substrate. As the ALP marks the antigen captured on the disk 311, the substrate (naphthyl phosphate) is converted to naphthol which is drawn through the biosensor 29 and oxidised on the porous graphite disk 313 by the potential difference applied thereto by the working electrode contact 303. Oxidation of the naphthol on the graphite disk 313 causes a flow of electrons (ie a current flowing in an electrical circuit comprising the counter electrode 301, aqueous solution, the working electrode 313, the working electrode contact 303 and connected devices) between the working electrode contact 303 and the counter electrode 301, the magnitude of the produced current being indicative of the quantity of naphthol oxidised at the graphite disk 313 and hence indicative of the quantity of antigen under test in the patient sample.

Whilst the above has been described in relation to an ALP enzyme and naphthyl phosphate pair, it will be understood that any enzyme-substrate combination may be used that produces a readily oxidisable or reducible species. For example, aminophenyl phosphate could be used as a substrate with ALP. Other examples of enzyme-substrate pairs are beta-galactosidase with p-Aminophenyl-beta-D-galactosidase to produce the electroactive species aminophenol, glucose oxidase with glucose to produce the electroactive species hydrogen peroxide and lactate dehydrogenase with lactate in the presence of $NAD^+$ to produce the electroactive species NADH.

Figure 9:
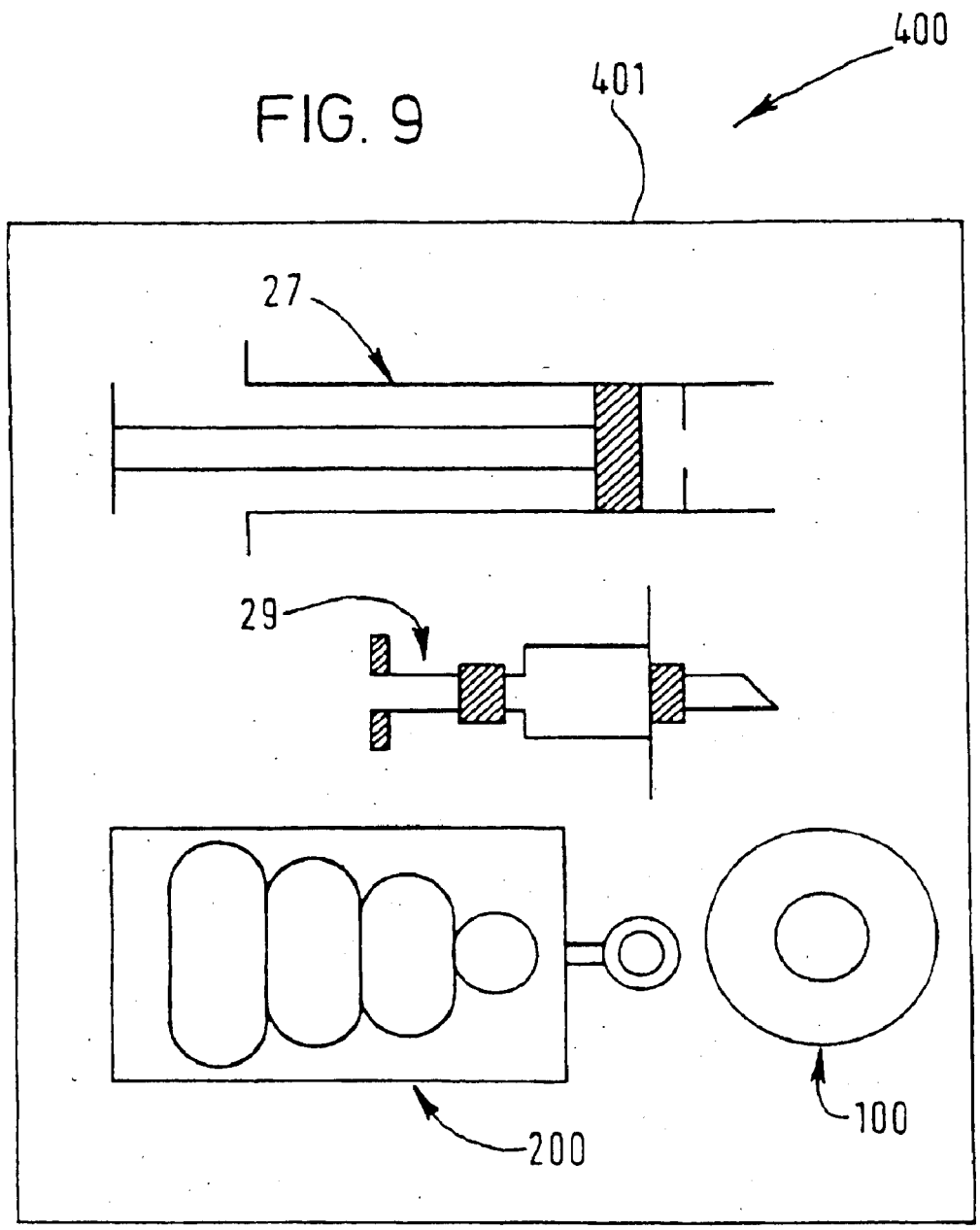
FIG. 9 is a plan view of a disposable diagnostic kit.

FIG. 9 is a plan view of a disposable diagnostic kit 400. The kit 400 is particularly suitable for use with the apparatus of FIG. 1. As shown in FIG. 9, the kit 400 comprises a container 401 within which there is provided a disposable sample container 100, a disposable syringe 27, a disposable biosensor 29 and a disposable reagent cartridge 200. The kit container 401 is provided with a removable sealed cover (not shown) which allows the sterility of the components to be maintained up to their point of use. As mentioned above, the kit 400 and its components may be manufactured at a relatively low cost from plastic material.

One highly preferred embodiment of the apparatus according to the invention will now be described. The temperature controlled block which holds the reagent strips and acts as a support for the centrifuge mechanism may be made from aluminium.

Each cartridge sensor may be a reflective optical device connected to the controller for indicating the presence of a cartridge to the microcontroller. The entire block is lifted by an up/down motor to enable sample or reagent to be drawn from the container or cartridge as required. This motor is mounted onto the a base of the apparatus.

The centrifuge is mounted on a sliding mechanism and positioned under each sensor by an index motor. The centrifuge consists of a holder into which the container is placed by the user and a guard ring to contain the container. A light sensing device is placed under the holder and interfaced to the controller to detect the presence of the sample (e.g. blood) filled container through light level changes.

The cartridges and container are positioned by a motor in a front to back direction. Since the sensor tip is fixed all samples are presented to the tip by the combination of motions of the forward/back motor, index motor and up/down motor.

The sensor system has a motor for each biosensor which drives the syringe pistori through a direct linkage, in either direction as required by the controller. The lower part of the drive assembly holds the biosensor in a fixed position and provides a guard for the electrical contacts to the biosensor. An LED indicator is positioned adjacent each biosensor to inform the user of that biosensor's status. The electrical contacts are mounted directly onto a signal processing board which interfaces with the controller and provides a voltage to the biosensors during an assay.

The apparatus is operated by selecting pre-programmed options presented by menus which appear on the display. Bar-codes on the syringe and cartridge also provide a means of selecting test type, batch or kit calibration data etc. The user is required to confirm the selection by keypad. A printer provides a hard copy of the result in either a text or graphical format. Should an error occur a single red LED lights and an audible alarm beeps while an error message is displayed.

A CCD (charge coupled device) type scanner reads Information from bar-codes on the kit components such as the biosensor/syringe and cartridge.

The kit also has a bar-code label for entering other data. Should the label be unreadable then data is entered manually through the keypad.

Data, sensor and control signal inputs are read by the controller and processed to determine the control and data output response. The apparatus is based upon a microcontroled integrated circuit which requires external data and program memory with extra I/O (input/output) capability. The data memory is non-volatile RAM (NVR) so patient identity and results are preserved as a database when the apparatus is shut down. A real time clock is resident within the NVR to provide date and time reference during testing. The various positioning and syringe drive motors are enabled and stepped by the controller via motor drive interfaces on the motor drive boards. Biosensor power and data conversion is carried out by the biosensor signal board under microcontroller supervision. Data for printout are sent to a printer interface board and which manages the printer operation. Block temperature is controlled by the microcontroller via the block heater which contains a temperature sensor and heater power control.

The apparatus and its components and signal elaboration software operate from mains power supplies via an IEC type inlet. The entire works and kit components are enclosed during the assay to prevent tampering The biosensor contains a porous disk which is impregnated with an assay specific material. Another disk in the biosensor (preferably a graphite disk) is in contact with conductive plastic parts which provide a path for current applied by the instrument during the test. Test kit reagents and sample are successively drawn through the cell by the action of the syringe piston. The speed of piston movement determines the flow rate which is controlled precisely by the controller. An air pocket inside the syringe damps drive movement to produce a smooth liquid flow through the cell. A potential is applied across the cell and the current flow measured. Analysis of this current gives the result of the assay. A bar code label is placed on the syringe to identify the assay, calibration data, batch/lot data and expiry.

The container is filled with sufficient sample (e.g. blood) to guarantee sufficient sample for three assays. High speeds are employed to produce a packed cell consistency to the haematocrit leaving plasma to be sampled. The shape of the centre of the container allows plasma to flow to the centre of the container for retention while keeping haematocrit in the outer region.

The reagent cartridge contains four compartments which hold the reagent for the assay. The reagent is sealed into the strip by a foil membrane which is pierced by the sensor tip during the assay. A bar-code is put on the strip to identify the type of assay and lot number.

Use of the Apparatus to Assess Acute Myocardial Infarction (AMI)

The cardiac marker proteins are proteins highly specific to myocardial tissue which are released into serum during AMI tissue damage. Some of these, such as CK-MB and Myoglobin, have now been clinically validated by many studies as specific and sensitive markers for AMI. Others e.g. Troponin are growing in popularity and there are many groups involved in trying to discover earlier and more sensitive markers.

Table 1 (below) summarises the most popular of the markers currently available and their main characteristics. Each of these markers has something slightly different to offer in diagnosis and therapy. Myoglobin with a molecular weight of 17,000 daltons is one of the first to appear in serum or plasma after the AMI event. However it returns to normal levels within 24 hours so is not useful in diagnosing a patient who has presented some time after the symptoms commenced but would help in the decision to start thrombolytic therapy for a patient who presents early.

TABLE 1

AMI ANALYTE PANEL

| Enzyme | Rise (h) | Peak (h) | Return to Normal (h) | Notes |
| --- | --- | --- | --- | --- |
| CK | 4–6 | 24 | 48 | Indicator of reperfusion |
| CK | 4–6 | 24 | 48 | Specific for myocardium Indicator of reperfusion |
| Myoglobin | 1–3 | 4–8 | 24 | Very rapid |
| Cardiac Myosin Light Chains (cMLC) | 2 | high levels stable for several days | 240 | Related to infarct size Elevated in Unstable Angina |
| Troponin (T and I) | 4–6 | 48–72 | 240 | Highly specific for myocardium Indicator of reperfusion |

Figure 10:
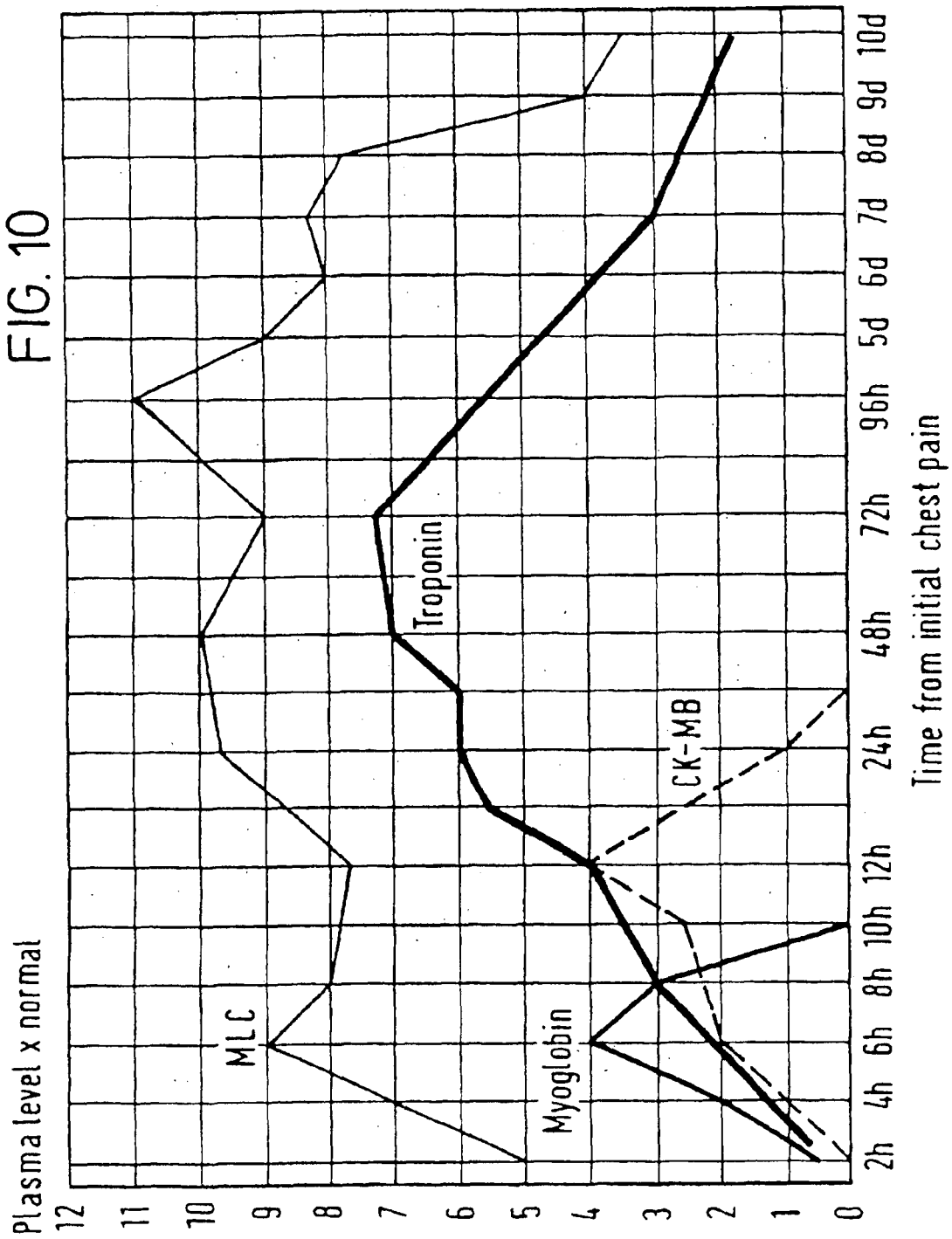
FIG. 10 is a graph.

To select the ideal parameters for a particular patient it is necessary to consider the general time course of these proteins in blood and their other characteristics. FIG. 10 shows typical behaviour with time of these markers in a patient's serum. In this regard FIG. 10 shows the concentration variation in serum with time after AMI for currently popular cardiac markers (see also FIG. 14 and FIG. 15).

The apparatus of the present invention will offer the possibility to log and to present the parameters in this graphical format which allows the clinician to closely follow the patient therapy, to monitor for second infarction and to detect successful reperfusion.

In a preferred embodiment, the first panel of instrument will have the parameters Myoglobin and CK-MB in the now acceptable (and increasingly preferred) mass format ($\mu$g/L). Many clinicians would traditionally request a total CK test as well as the CK-MB. Comparing CK-MB ratio to CK (when both are U/L) is a recommended criterion of the World Health Organisation (AMI if CK-MB/CK>4%).

The apparatus of the present invention provides a means of determining total CK as an activity measurement or an estimate of total CK. In this regard, the total CK content of serum is largely composed of the isoforms CK-MM and CK-MB and the brain enzyme CK-BB is not present in significant quantities unless there is severe head injury. For example see FIG. 11 which is an electrophoresis separation to illustrate CK isoforms in serum and brain extract. In these CK electrophoretograms, a=total brain extract: b=serum sample from a patient with an infarction: c=extract from the cortex of the brain: d=extract from the medulla of the brain: e=extract from the cerebellum (agarose electrophoresis 50 mM sodium barbital buffer (pH 8.0). 85 V). Thus in effect the measurement of CK-BB is not effective during AMI. A graph of CK-MB levels and CK-BB levels against time in the serum of a patient during AMI in FIG. 12 also illustrates this. In this regard, FIG. 12 is an illustration of CK-MB and CK-BB levels measured by two site immunoassay over time in serum from a patient suffering from AMI.

In particular FIG. 12 shows a typical curve showing increase in serum CK-MB with time after myocardial infarction. As can be seen, both CK-MM and CK-MB elevate during AMI although the proportion of CK-MB to MM rises due to the high amounts of CK-MB in heart tissue. CK-MM however can also be elevated after muscle trauma as can CK-MB to a lesser extent. In practice measurement of CK-MM+CK-MB will effectively give the total CK in serum. Normally total CK is measured by clinical chemistry.

There are also been studies of the various isoforms in serum and how they change with time. Three types of MM exist—namely MM1, MM2 and MM3—and two types of MB exist—namely MB1 and MB2. These are normally quantified by high voltage electrophoresis and fluorescent staining but some immunoassays are becoming available. The ratios of the MB1/MB2 and MM1/MM3 also help in the early diagnosis of AMI but some studies claim that total CK-MB measurement is just as effective. There seem to be no studies of the total CK-MB CK-MM ratio. However, the apparatus of the present invention would be capable of performing such a study and which in theory would be very specific for AMI (setting a threshold ratio for positive diagnosis).

For the preferred apparatus and cartridge of the present invention the most convenient method will be to supply tests for myoglobin, CK-MB and CK-MM all as mass assays (via two-site immunoassay). It is quite possible that the users will use only CK-MB and Myoglobin for the majority of the patients but if they require total CK they have the option of loading to load both CK-MB and CK-MM, cartridges in one run. The instrument will give back values for CK-MM, CK-MB and estimate total CK and the CK-MB total CK ratio. Alternatively CK-MM can be measured on its own by the instrument.

Myoglobin remains the parameter of choice for early diagnosis of AMI—increasing in the first 1–3 hours after AMI, peaking around 6 hours after and returning to normal within 24 hours. The current threshold for AMI with Myoglobin is >90 $\mu$g/L although this could be clinically verified using the apparatus of the present invention.

CK-MB threshold levels for AMI have been set at around 5 $\mu$g/L in other manufacturer's kits.

Both CK-MB and Myoglobin can be used to monitor reperfusion. FIG. 13 shows the difference between reperfused and non-reperfused CK-MB levels in two patients after rt-PA therapy.

In this regard, FIG. 13 illustrates CK-MB measurement with time in reperfused patients and non-reperfused patients, wherein serial total CK (left) and CK-MB (right) values for two patients following myocardial infarction: one successfully reperfused after recombinant tissue-type plasminogen activator (rt-PA) therapy (reperfusion): one not reperfused.

In summary, therefore, the biosensor system of the present invention allows sensitive immunoassays to be performed in less than 15 minutes in the ward or satellite laboratory. The present invention is particularly of use in the areas of emergency cardiology, critical care units and other departments concerned with the diagnosis and treatment of acute myocardial infarction (AMI). In a preferred embodiment, the system is capable of performing up to three immunoassay parameters simultaneously on one patient sample in less than fifteen minutes. In the cardiology sector the instrument will act as a diagnostic aid for AMI and as a means of monitoring reperfusion. In a preferred embodiment, the three parameters offered on the first panel will be myoglobin, CK-MB and CK-MM (for total CK).

The instrument of the present invention can be small and light, and can be easily carried around a ward to different locations or suitable for transportation on a small trolley. Typically, an operator will load 3 mls of heparinised blood from the patient into a disposable plastic rotor which is then placed in the machine. For each parameter there is a small syringe and reagent cartridge which will be packaged together and bar coded for a specific test (myoglobin, CK-MB etc.). The operator uses a wand—type bar code reader to swipe the details from the side of the syringe and the machine lights up an LED where the syringe is to be loaded and checks on the display that the operator wants to test this parameter for the current patient sample. This is repeated for the cartridge. One, two or three parameters can be run 3 for any patient sample in one cycle of the machine.

When the lid of the instrument is closed the apparatus goes into its routine. Typically, the blood is centrifuged for 4 minutes and during that time the instrument is priming and checking the electrochemical biosensors.

At the end of the period typically 250 $\mu$l of plasma is aspirated directly from the disposable rotor into each of the syringe heads. In a preferred embodiment the plasma passes through the syringe head it traverses a porous antibody-coated membrane and the antigen being tested is captured. The syringe then goes to the cartridge and typically draws up 500 $\mu$l of tracer antibody conjugated to alkaline phosphatase (ALP). This passes through the membrane marking the captured antigen.

In this preferred embodiment, the syringe next draws up wash solution (1 ml) and then goes to the enzyme substrate well on the cartridge. Inside the syringe head (behind the antibody-coated membrane) is a porous electrode with a second return electrode located further along the head. The ALP substrate used is electrochemical in that contact with ALP converts the substrate (naphthyl phosphate into an electroactive product (naphthol) which is easily oxidised on the porous electrode. The assay is calibrated for each antigen so that current at the electrode corresponds to antigen concentration.

Typically, all three parameters are completed within 15 min and the instrument will display concentrations, print out concentrations on request and also print graphs for each parameter against time if previous values have been stored for that patient.

In a preferred embodiment, the instrument is capable of storing 24 values for each of the three parameters for up to a maximum of 15 patients.

Thus, the apparatus of the present invention uses an in vitro electrochemical assay technique to determine heart attacks by measuring the levels of specific markers in a patient's or victim's blood sample. The levels of markers indicate the time and severity of the attack and also the progress of recovery.

Thus, also, the apparatus of the present invention is an instrument into which one use disposable kit components and blood sample are loaded in order to obtain a result. The kit components consist of an electrochemical cell and syringe, a reagent strip and a sample holder (otherwise known as a centrifuge rotor).

The syringe and strip are bar-coded for correct identification and assay/calibration data. Each marker requires a specific type of cell.

The apparatus of the present invention performs the assay automatically once the assay kit components have been loaded and verified by the bar-code matching and the operators confirmation. The patients blood is measured into the rotor and loaded onto the instrument at the beginning of the test. The assay is performed automatically and results are stored internally for display or printout as required.

It will be understood that the present invention has been described herein by way of example only and that modifications and additions may be made within the scope of the invention.

What is claimed is:

1. An automatic diagnostic apparatus comprising:
   a controller for controlling operation of the apparatus and for processing data;
   a sample container comprising a substantially frusto-conical outer wall an a substantially conical inner wall, each having a narrow end and a broader end;
   the outer wall having a lip at its narrow end and connecting with a subtantially planar annular first base at its broader end;
   the substantially conical inner wall connecting at its broader end with inner edge of the annular first base and connecting at its narrow end with a depression;
   a rack and platform system including a rotor motor which is operable to spin the sample container to cause heavier components of a sample therein to move toward the first base and lighter components to move up the inner wall to the depression;
   a sensing system, which is a syringe and biosensor system comprising electrochemical immunoassay biosensor for performing an electrochemical immunoassay of the lighter components of the sample, and a syringe comprising a syringe body and a plunger effective to draw a sample and, optionally, a reagent in and through the biosensor;
   voltage supply means for applying a potential difference to said sensing system; and
   output means for communicating processed data to a user.

2. An automatic diagnostic apparatus according to claim 1, wherein:
   the sensing system has a motor arm;
   the syringe has a base and two ends, one end of which is in communication with the motor arm, and the other end of which internally abuts the syringes base.

3. An automatic diagnostic apparatus according to claim 1, wherein the rack and platform system comprises a block with three shaped apertures for securely holding a reagent cartridge.

4. An automatic diagnostic apparatus according to claim 1 further comprising a reagent cartridge having a substantially planar body with four reagent compartments depending therefrom and having a surface; the reagent compartments being open at the surface of the planar body.

5. An automatic diagnostic apparatus according to claim 4, wherein the reagent cartridge is filled with a reagent for testing myocardial infarction.

6. An automatic diagnostic apparatus according to claim 4, wherein one of the reagent compartments is filled with alkaline phosphatase, a second reagent compartment is filled with a dried naphthyl phosphate, a third reagent compartment is filled with a wash solution, and the fourth reagent compartment is filled with a buffer solution.

7. An automatic diagnostic apparatus according to claim 1, wherein the rack and platform system is provided with an up/down motor and a forward/backward motor.

8. An automatic diagnostic apparatus according to claim 1, wherein the biosensor comprises a counter electrode, a working electrode contact a biosensor body, a biosensor inlet and a solid phase immunoassay site comprising a porous spacer disk, a porous PVDF disk and a porous graphite disk as a working electrode.

9. An automatic diagnostic apparatus according to claim 8, wherein the porous PDVF disk is impregnated with an antibody.

* * * * *